(12) United States Patent
Rudy et al.

(10) Patent No.: US 7,016,719 B2
(45) Date of Patent: Mar. 21, 2006

(54) SYSTEM AND METHODS FOR NONINVASIVE ELECTROCARDIOGRAPHIC IMAGING (ECGI) USING GENERALIZED MINIMUM RESIDUAL (GMRES)

(75) Inventors: Yoram Rudy, Shaker Heights, OH (US); Charulatha Ramanathan, Richmond Heights, OH (US); Raja Ghanem, Cleveland Heights, OH (US); Ping Jia, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 524 days.

(21) Appl. No.: 10/264,572

(22) Filed: Oct. 4, 2002

(65) Prior Publication Data

US 2003/0120163 A1 Jun. 26, 2003

Related U.S. Application Data

(63) Continuation-in-part of application No. 10/037,603, filed on Oct. 19, 2001, now Pat. No. 6,772,004, which is a continuation of application No. 09/463,428, filed as application No. PCT/US98/15927 on Jul. 29, 1998, now abandoned.

(60) Provisional application No. 60/327,419, filed on Oct. 4, 2001, provisional application No. 60/054,342, filed on Jul. 31, 1997.

(51) Int. Cl.
*A61B 5/04* (2006.01)

(52) U.S. Cl. .................................................... 600/513
(58) Field of Classification Search ................. 600/425, 600/411, 513, 547, 523, 509; 128/920, 922
See application file for complete search history.

(56) References Cited

U.S. PATENT DOCUMENTS

| | | |
|---|---|---|
| 3,848,582 A | 11/1974 | Milani et al. |
| 3,858,578 A | 1/1975 | Dehnert et al. |
| 4,033,336 A | 7/1977 | Murawski et al. |
| 4,183,354 A | 1/1980 | Sibley et al. |
| 4,203,451 A | 5/1980 | Panico |
| 4,535,783 A | 8/1985 | Marangoni |
| 4,593,698 A | 6/1986 | Athans |
| 4,606,352 A | 8/1986 | Geddes et al. |
| 4,805,631 A | 2/1989 | Roi du Maroc, II |
| 4,858,617 A | 8/1989 | Sanders |
| 4,989,611 A | 2/1991 | Zanetti et al. |
| 4,991,580 A | 2/1991 | Moore |
| 4,991,587 A | 2/1991 | Blakeley et al. |
| 5,020,540 A | 6/1991 | Chamoun |
| 5,038,791 A | 8/1991 | Collins et al. |
| 5,042,499 A | 8/1991 | Frank et al. |

(Continued)

OTHER PUBLICATIONS

Non-negativity and iterative methods for ill-posed problems D Calvetti, G Landi, L Reichel and F Sgallari 2004 Inverse Problems 20 1747-1758.*

(Continued)

*Primary Examiner*—Robert Pezzuto
*Assistant Examiner*—Jason Rosenzweig
(74) *Attorney, Agent, or Firm*—Scott E. Kamholz; Foley Hoag LLP

(57) ABSTRACT

Methods and systems for computing epicardial surface electric potentials based on measured body surface electric potentials, where the methods and systems include representing at least one geometric relationship between at least one body surface electric potential measuring system and the epicardial surface as a multidimensional matrix, estimating an inverse of the multidimensional matrix based on a Generalized Minimum Residual (GMRes) method, and, based on the inverse matrix and the measured body surface potentials, determining the epicardial surface electric potentials.

21 Claims, 15 Drawing Sheets

U.S. PATENT DOCUMENTS

| | | | |
|---|---|---|---|
| 5,086,776 A | 2/1992 | Fowler, Jr. et al. | |
| 5,151,856 A | 9/1992 | Halmann et al. | |
| 5,161,539 A | 11/1992 | Evans et al. | |
| 5,205,295 A | 4/1993 | Del Mar et al. | |
| 5,311,867 A | 5/1994 | Kynor | |
| 5,311,873 A | 5/1994 | Savard et al. | |
| 5,343,870 A | 9/1994 | Gallant et al. | |
| 5,433,198 A | 7/1995 | Desai | |
| 5,433,209 A | 7/1995 | Gallant et al. | |
| 5,483,968 A | 1/1996 | Adam et al. | |
| 5,487,391 A | 1/1996 | Panescu | |
| 5,503,149 A | 4/1996 | Beavin | |
| 5,503,158 A | 4/1996 | Coppock et al. | |
| 5,568,809 A | 10/1996 | Ben-haim | |
| 5,606,978 A | 3/1997 | Armstrong et al. | |
| 5,687,737 A | 11/1997 | Branham et al. | |
| 5,848,972 A * | 12/1998 | Triedman et al. | 600/508 |
| 5,947,899 A | 9/1999 | Winslow et al. | |
| 6,014,582 A | 1/2000 | He | |
| 6,052,618 A | 4/2000 | Dahlke et al. | |
| 6,256,540 B1 * | 7/2001 | Panescu et al. | 607/122 |
| 6,278,894 B1 * | 8/2001 | Salo et al. | 600/547 |
| 6,349,272 B1 * | 2/2002 | Phillips | 703/2 |
| 6,370,435 B1 * | 4/2002 | Panescu et al. | 607/122 |
| 6,487,441 B1 * | 11/2002 | Swanson et al. | 600/510 |
| 6,516,220 B1 * | 2/2003 | Selvester et al. | 600/523 |
| 6,522,905 B1 * | 2/2003 | Desai | 600/374 |
| 6,772,004 B1 * | 8/2004 | Rudy | 600/509 |
| 6,810,370 B1 * | 10/2004 | Watts, III | 703/10 |
| 6,856,830 B1 * | 2/2005 | He | 600/513 |
| 2003/0120163 A1 * | 6/2003 | Rudy et al. | 600/509 |
| 2004/0082870 A1 * | 4/2004 | Rudy et al. | 600/509 |

OTHER PUBLICATIONS

Rudy Y., "The Inverse Problem in Electrocardiography Solutions in Terms of Epicardial Potentials": CRC Critical Reviews in Biomedical Engineering, 16:215-268 (1988).

Rudy, Y., et al., "The Electrocardiographic Inverse Problem," Critical Reviews in Biomedical Engineering, 20:25-46 (1992).

Messinger, et al., "Computational Issues of Importance to the Inverse Recovery of Epicardial Potentials in a Realistic Heart-Torso Geometry," Math Biosci, 97:85-120 (1989) (published erratum in Math Biosci 99 (1): 141 (Apr. 1990).

Oster, et al., "The Use of Temporal Information in the Regularization of the Inverse Problem of a Electrocardiography," IEEE Transactions on Biomedical Engineering, 39:65-75 (1992).

P. Colli Franzone, et al., "A Mathematical Procedure for Solving the Inverse Potential Problem of Electrocardiography," Mathematical Biosciences 77:353-396 (1985).

P. Colli Franzone, et al., "Finite Element Approximation of Regularized Solutions of the Inverse Potential Problem of Electrocardiography and Applications to Experimental Data", Calcolo 22:91-186 (1985).

Taccardi, et al., "Effect of Myocardial Fiber Direction on Epicardial Potentials", Circulation, 90:3076-90 (1994).

Rudy, Y., et al., "Noninvasive Electrocardiographic Imaging," Annals of Noninvasive Electrocardiology, vol. 4, No. 3, Jul. 1999 (Futura Publishing Company, Inc., Armonk, NY).

Oster, et al., "Noninvasive Electrocardiographic Imaging—Reconstruction of Epicardial Potentials, Electrograms, and Isochones and Localization of Single and Multiple Electrocardiac Events", Circulation, vol. 96, No. 3, Aug. 5, 1997.

Oster, et al., "Electrocardiographic Imaging—Noninvasive Characterization of Intramural Myocardial Activation From Inverse-Reconstructed Epicardial Potentials and Electrograms", Circulation, 1998; 97, Apr. 21, 1998, pp. 1496-1507.

Oster, et al., "Electrocardiographic Imaging of Electrophysiologically Abnormal Substrates in Infarcted Hearts—A Model Study", Circulation, 2000: 101, Feb. 8, 2000, pp. 533-540.

Rudy, Y., et al., "Noninvasive Imaging and Catheter Imaging of Potentials, Electrograms, and Isochones on the Ventricular Surfaces," Journal of Electrocardiology, vol. 30 Supplement (1998) pp. 19-23.

Oster, et al., "Regional Regularization of the Electrocardiographic Inverse Problem: A Model Study Using Spherical Geometry," IEEE Transactions on Biomedical Engineering, vol. 44, No. 2, Feb. 1997, pp. 188-199.

Burnes, J., et al., "A Field-Compatible Method for Interpolating Biopotentials", Annals of Biomedical Engineering, vol. 26, pp. 37-47, 1998.

Burnes, J., et al., "A Noninvasive Imaging Modality for Cardiac Arrhythmias", Circulation, vol. 2102, No. 17, Oct. 24, 2000, pp. 2152-2158.

Ramanathan, C., et al., "Electrocardiographic Imaging: I. Effect of Torso Inhomogeneities on Body Surface Electrocardiographic Potentials", Journal of Cardiovascular Electrophysiology, vol. 12, No. 2, Feb. 2001, pp. 229-240.

Ramanathan, C., et al., "Electrocardiographic Imaging: II. Effect of Torso Inhomogeneities on Noninvasive Reconstruction of Epicardial Potentials, Electrograms, and Isochrones", Journal of Cardiovascular Electrophysiology, vol. 12, No. 2, Feb. 2001, pp. 241-252.

Burnes, J., et al., "Imaging Dispersion of Myocardial Repolarization, I Comparison of Body-Surface and Epicardial Measures", Circulation, vol. 104, No. 11, Sep. 11, 2001, pp. 1299-1305.

Ghanem, R., et al., "Imaging Dispersion of Myocardial Repolarization, II Noninvasive Reconstruction of Epicardial Measures", Circulation, vol. 104, No. 11, Sep. 11, 2001. pp. 1306-1312.

Ghanem, R., et al., "Electrocardiographic Imaging: Noninvasive Reconstruction of Epicardial Measures of Dispersion of Repolarization," Biomedizinische Technik, vol. 46, Supp. 2, 2001, pp. 201-203.

Burnes, J., et al., "Noninvasive ECG Imaging of Substrate and Intramural Ventricular Tachycardia in Infarcted Hearts," Journal of the American College of Cardiology, Dec., 2001, in press.

Tikhonov, A., et al., "Solutions of Ill-Posed Problems", Chapter II. "The Regularization Method", 1977 V.H. Winston & Sons, Washington, D.C., A Halsted Press, John Wiley & Sons, pp. 45-62.

Brebbia, C., et al., "Boundary Element Techniques—Theory and Applications in Engineering", Springer-Verlag, 1984, pp. 127-137.

Brebbia, C., et al., "Boundary Elements An Introductory Course," Computational Mechanics Publications, Southampton, Boston, pp. 87-90.

Jackson, John D., "Classical Electrodynamics," Second Edition, John Wiley & Sons, pp. 39-43.

* cited by examiner

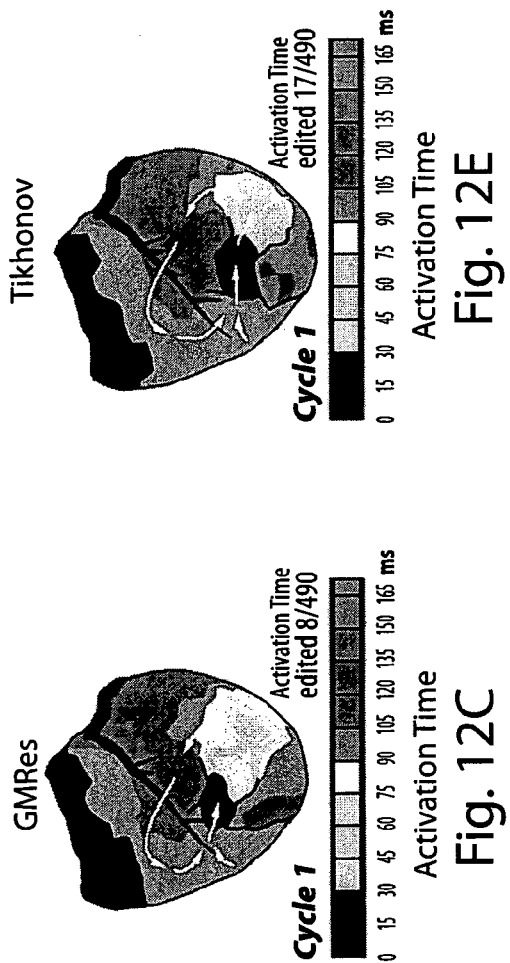
Fig. 12C
Fig. 12E
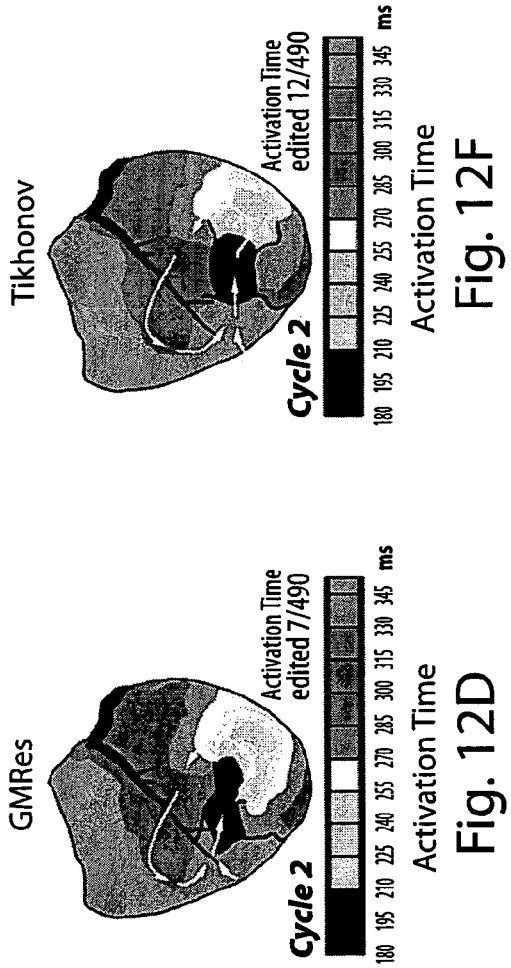
Fig. 12D
Fig. 12F
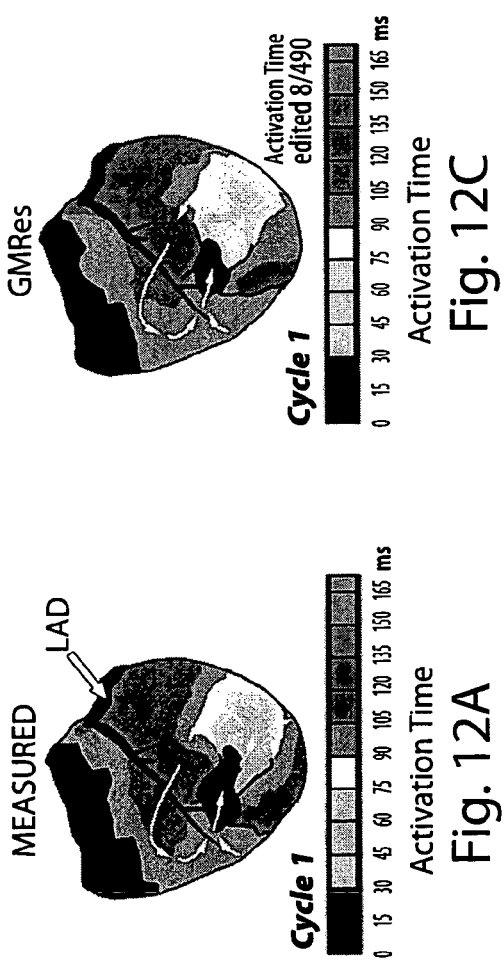
Fig. 12A
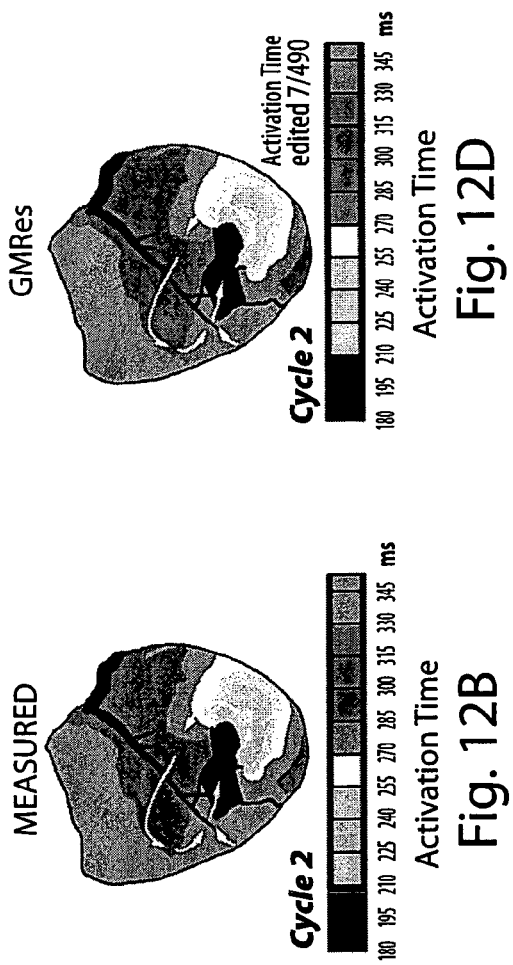
Fig. 12B

SYSTEM AND METHODS FOR NONINVASIVE ELECTROCARDIOGRAPHIC IMAGING (ECGI) USING GENERALIZED MINIMUM RESIDUAL (GMRES)

CLAIM OF PRIORITY

This application claims benefit to U.S. Ser. No. 60/327,419, entitled "Noninvasive Electrocardiographic Imaging (ECCI": filed on Oct. 4, 2001, and is a continuation-in-part of U.S. Ser. No. 10/037,603, filed on Oct. 19, 2001, now as U.S. Pat. No. 6,772,004, which is a continuation of Ser. No. 09/463,428 filed Mar. 29, 2000, now abandoned, which is a 371 of PCT/US98/15927 filed Jul. 29, 1998, which claims benefit of Ser. No. 60/054,342 with a filing date of Jul. 31, 1997, where the contents of all aforementioned provisional and non-provisional U.S. and PCT applications are incorporated herein by reference in their entirety.

STATEMENT OF GOVERNMENT INTEREST

The contents of this disclosure were supported by NIH-NHLBI Grant R37-HL-33343.

BACKGROUND (1) Field

The disclosed methods and systems relate generally to electrocardiographic imaging, and more particularly to methods and systems for noninvasive reconstruction of cardiac potentials, electrograms, and isochrones (activation patterns) in electrocardiographic imaging.

(2) Description of Relevant Art

Imaging and diagnosing cardiac electrical activity can be problematic because the electrical activity is time dependent and spatially distributed throughout the myocardium. Electrocardiographic techniques that include, for example, electrocardiograms (ECG) and vectorcardiography (VCG) can be limited in their ability to provide information and/or data on regional electrocardiac activity. These methods can also fail to localize bioelectric events in the heart.

Simultaneous recordings of potentials at tens or hundreds of locations on the torso, for example, can provide body surface potential maps (BSPMs) over the torso surface. Although the BSPMs can indicate regional cardiac electrical activity in a manner that may be different from conventional ECG techniques, these BSPM techniques generally provide a comparatively low resolution, smoothed projection of cardiac electrical activity that does not facilitate visual detection or identification of cardiac event locations (e.g., sites of initiation of cardiac arrhythmias) and details of regional activity (e.g., number and location of arrythmogenic foci in the heart).

In comparison, potential distributions measured on and over the epicardial surface of the heart can provide comparatively more accurate and higher resolution data that reflects electrical events within the myocardium. Accordingly, the study of cardiac excitation and arrhythmogenesis, for example, often rely upon the mapping of potentials directly from the epicardium.

With an increasing use of nonpharmacological anti-arrhythmic interventions (e.g., ablation), comparatively rapid and accurate localization of electrocardiac events can be beneficial. Electrocardiographic imaging (ECGI) is a non-invasive imaging modality for cardiac electrophysiology (EP) and arrhythmias that can be used to reconstruct epicardial potentials and to provide electrograms and isochrones from, for example, BSPMs and/or other electrocardiographic body surface potentials.

SUMMARY

The disclosed methods and systems include a method for computing epicardial surface electric potentials based on measured body surface electric potentials, the method also including representing at least one geometric relationship between at least one body surface electric potential measuring system and the epicardial surface as a multidimensional matrix, using a Generalized Minimum Residual (GMRes) method to estimate an inverse of the multidimensional matrix, and, based on the inverse matrix and the measured body surface potentials, determining the epicardial surface electric potentials. Representing the geometric relationship can include measuring the position of the at least one body surface electric potential measuring system and/or measuring the position of at least one electrode, which can also include providing at least one of a CT scan, a MRI, an X-ray, and an X-ray. Representing the geometric relationship can also include determining an epicardial envelope and/or employing a boundary element method.

Usine a GMRes method can include determining a number of iterations for the GMRes method, which can include providing a maximum number of iterations for the GMRes method, collecting data from the maximum number of iterations, and based on the data from the maximum number of iterations, determining a number of iterations for the GMRes method. In one embodiment, determining a number of iterations includes comparing residual error to a Hessenberg matrix condition, and computing at least one of a corner of a condition L curve and a maximum curvature of a condition L curve. In some embodiments, determining a number of iterations includes determining a number of iterations based on at least one of: a corner of a condition L curve, a corner of an L curve, an increase in spatial frequency of a reconstructed potential map, and an increase in amplitude of a solution norm.

Using a GMRes method can include providing an initial condition of zero, and/or providing an initial condition based on a Tikhonov regularization of the multidimensional matrix.

Also disclosed is a method for computing electric potentials on an epicardial surface of a patient, where the method includes measuring electric potentials on the patient's body surface, expressing a geometrical relationship between the patient's body surface and the epicardial surface as a multi-dimensional matrix, determining an approximation of the two-dimensional matrix based on a Generalized Minimum Residual (GMRes) method, and, computing the electric potentials on the epicardial surface based on the approximated inverse and the measured electric potentials. Measuring electric potentials includes measuring electric potentials using a torso vest, where the torso vest includes electrodes. Other techniques for measuring electric potentials can be used, where such techniques can include at least one electrode.

In expressing a geometric relationship, the method can include measuring a location of at least one electrode, where the at least one electrode provides electric potential measurements of the patient's body surface. Such expression of a geometric relationship can also include measuring a location of the patient's epicardial envelope, and/or employing a boundary element method. The data upon which a geometric relationship can be expressed can include data associated with the patient, where the data can be obtained from at least one of CT scan data, MRI data, and X-ray data. Determining an approximation includes providing an initial condition based on at least one of a zero value and a Tikhonov regularization of the multi-dimensional matrix. Determining an approximation includes determining a number of iterations based on a residual error and a Hessenberg matrix condition.

Other objects and advantages will become apparent hereinafter in view of the specification and drawings.

BRIEF DESCRIPTION OF THE DRAWINGS

FIGS. 12a and 12b show isochrones constructed from measured electrograms;

FIGS. 12c and 12d show isochrones based on GMRes reconstruction;

FIGS. 12e and 12f show isochrones based on Tikhonov reconstruction;

DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the disclosed systems or methods.

The disclosed methods and systems employ a generalized minimal residual (GMRes) method and system to utilize electrocardiographic image (ECGI) data derived from body surface potential maps (BSPMs) to reconstruct epicardial potentials, which may be used to provide electrograms and isochrones. Those of ordinary skill in the art will recognize, however, that the methods and systems are not limited to BSPMs, and/or can employ electrocardiographic data, vectorcardiogram data, or combinations thereof, and although the disclosed methods and systems present electrograms and isochrones, other and/or additional data representations can be implemented.

Figure 1:
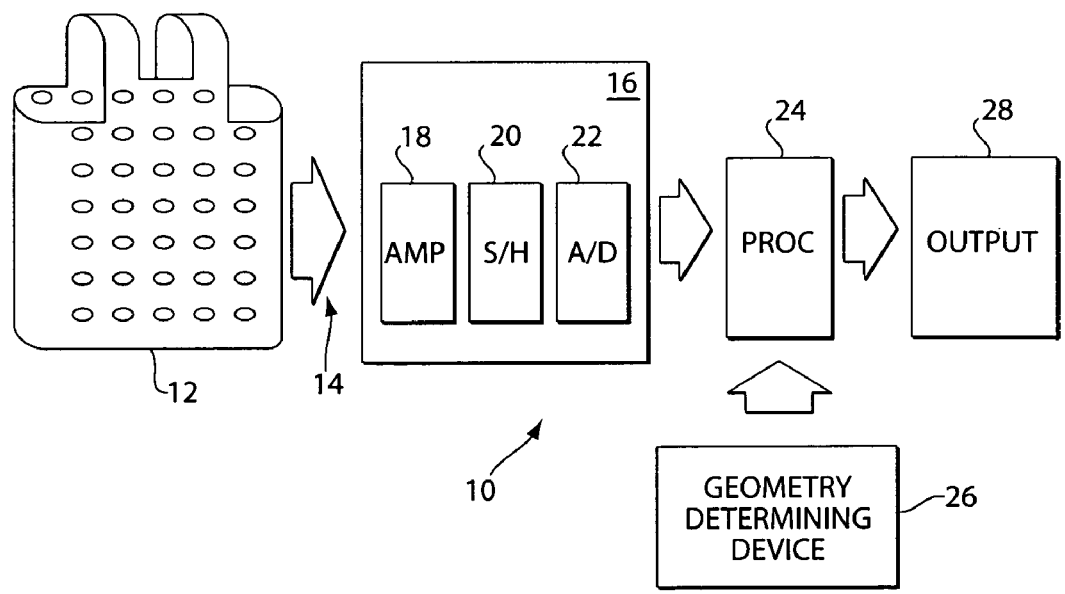
FIG. 1 illustrates a block diagram for obtaining data from an electrode vest.

FIG. 1 provides one illustration of a system according to the disclosed methods. The FIG. 1 system 10 includes one exemplary electrode vest 12 that can include electrodes that are disposed and/or positioned within the vest 12 to provide measurements of electrical potentials across a torso (front, back, sides, etc.) when positioned on a patient, for example. The vest 12 can be connected 14 to a device 16 that can include a processor and/or circuitry (e.g., hardware and/or software) for receiving data and processing data from the vest 12 via the connection 14. In the illustrated system, the device 16 includes an amplifier 18, a sample and hold 20, and analog to digital converter 22. As provided herein, those of ordinary skill will recognize that the device 16 may be incorporated with the vest 12 in some embodiments. In the FIG. 1 system, the device 16 can provide or otherwise communicate data to a processor 24 or processor-controlled device, as provided herein. Further, the illustrated processor 24 can receive data from a geometry determining device 26. The processor 24 can include instructions and/or be coupled with hardware for processing the data from the vest 12 and the geometry determining device 26 as provided herein, and additionally and optionally can communicate such processed data to one or more output devices 28. Those of ordinary skill will recognize that the output device 28 can be a display, printer, and/or other device that can be integrated with or otherwise be in communications with the processor 24.

In an embodiment, the FIG. 1 system 10 can be an online and/or integrated channel system that can be a stand-alone and portable unit with data acquisition and data processing capabilities. Further, in one embodiment, the illustrated vest 12 can include approximately two-hundred forty silver/silver chloride (Ag/AgCl) electrodes for acquiring electrocardiograph (ECG) signals from a body surface such as a torso. Those of ordinary skill will recognize that the vest 12 can include other numbers of electrodes, including for example, in the range from approximately one-hundred twenty to two-hundred fifty, although fewer or more electrodes can be used depending upon the application. Further, although the use of silver/silver chloride electrodes allows the electrodes to be used without gel and thus may decrease the number of electrodes that may short circuit and may allow for rapid application of the electrodes to the patient, other systems that utilize gel and/or other non-gel systems can be used.

The illustrated vest 12 may also provide two-dimensional stability to the electrode array so that electrode spacing can be maintained substantially constant and electrode positions can be determined as provided herein. The vest 12, connector 14, and/or device 16 can further include comparatively high-input resistance amplifiers (e.g., on the order of $10^{12}$ ohm) and driven shield electrode cables to provide increased common mode rejection. For example, in one embodiment, driven shield cables can be coaxial cables that can be optically coupled to avoid shock to the patient, while other types of electrode arrangements and/or methods and systems to obtain body surface potentials may be used. Those of ordinary skill will thus understand the vest 12, connector 14, and device 16 to more generally be a body surface potential measurement system and/or device that provides or otherwise communicates (e.g., via wired or wireless network, direct communications, etc.) body surface potential data to the processor 24, where such data can be in a format that is compatible for receipt by the processor 24. In an embodiment, the illustrated body surface potential measurement system 12, 14, 16 can be employed for body surface mapping, epicardial mapping (e.g., using epicardial electrodes), endocardial mapping, and/or intracavitary mapping using a multi-electrode probe.

Figure 2:
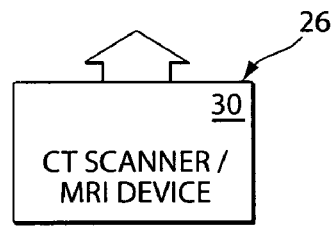
FIG. 2 illustrates one geometry determining device.

Referring again to FIG. 1, the geometry determining device 26 can be a system and/or device for providing geometric data for an anatomical part(s) such as the heart, and accordingly, the device 26 can include a system that provides x-ray, ultrasound, computed tomography (CT), and/or magnetic resonance imaging (MRI) data. For example, as shown in FIG. 2, the geometry determining device 26 may be a CT scanner or MRI device 30. In an embodiment according to FIGS. 1 and 2, the illustrated CT scanner/MRI device 30 can generate data, which can be image data, to determine torso geometry and, consequently, body surface electrode positions. The device 30 can also provide data associated with an epicardial envelope surrounding the heart, where those of ordinary skill understand that the epicardial envelope can provide an estimate of the epicardial surface. Further, locating the epicardial envelope or surface can include determining or otherwise providing data to be associated with the location of the heart. In an exemplary system that utilizes a CT scanner 30, the scanner 30 can provide slice thickness between one and eight millimeters and can have adjustable kVp and mAs settings to perform different types of CT scans of different parts of a patient's body.

Figure 4:
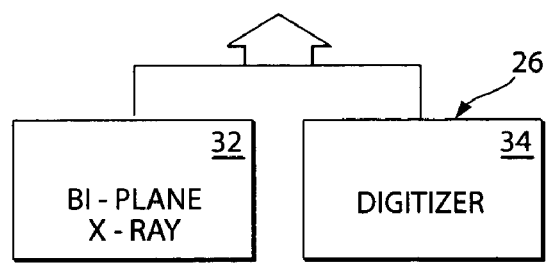
FIG. 4 illustrates other geometry determining devices.
Figure 3:
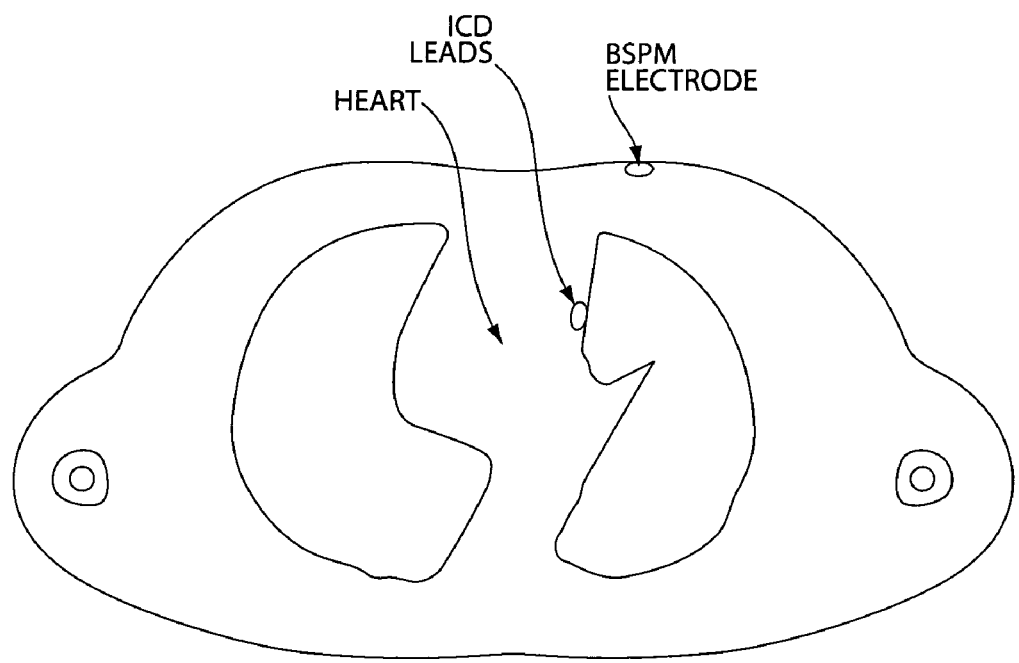
FIG. 3 illustrates a CT scan.

FIG. 4 presents an embodiment having a geometry device 26 that includes a system that includes a bi-plane or single plane x-ray fluoroscopy machine 32 and a digitizer 34. The FIG. 4 embodiment can utilize a three dimensional digitizer/locator 34 to obtain a patient's torso geometry and/or positions of body surface electrodes. In a system according to FIG. 4, an epicardial envelope can be constructed from two bi-planar x-rays using curve fitting techniques, although other techniques can be used.

FIG. 5(*a*) provides one illustrative embodiment for a processor 24 according to FIG. 1. Accordingly, in an embodiment based on FIG. 1, the geometry determining device 26 can provide the processor 24 with data associated with the geometry of the torso and vest, including for example electrode position, and the epicardial envelope (or surface). As provided herein, the geometry determining device (e.g., CT, x-ray system, etc.) can provide data for determining or otherwise provide data associated with a geometric envelope that approximates the epicardium to allow or otherwise facilitate a geometric relationship between the epicardial envelope surrounding the heart and electrode positions (or torso geometry) 141. A matrix of coefficients, A, can also be generated 142 to express the relationship between epicardial surface and body surface. The matrix A can thus be understood to be a geometry and conductivity transfer matrix that represents properties of the volume conductor between the body surface and epicardial surface.

Referring again to FIG. 5a, electric potentials measured on the torso surface can be input to or otherwise provided to the processor 24 from the vest 12 or other device that provides electrical potentials, where in the FIG. 5a embodiment, the processor can store 143 such electrical potentials. The processor 24 can then cause epicardial potentials to be determined 144 based on the aforementioned electrical potentials and matrix of coefficients, A. As provided previously herein, based on the epicardial potentials, electrograms and isochrone maps can be generated for display and evaluation 145.

Figure 5A:
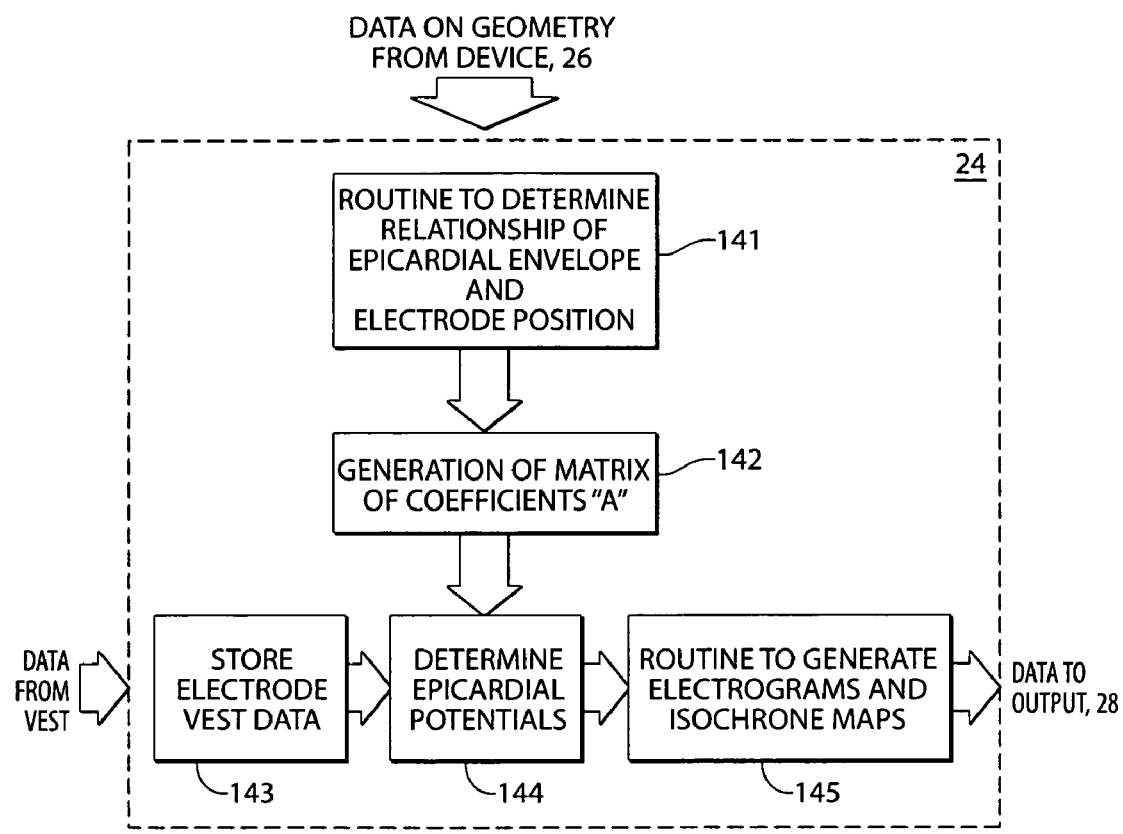
FIG. 5a is an exemplary block diagram for determining epicardial potentials.
Figure 5B:
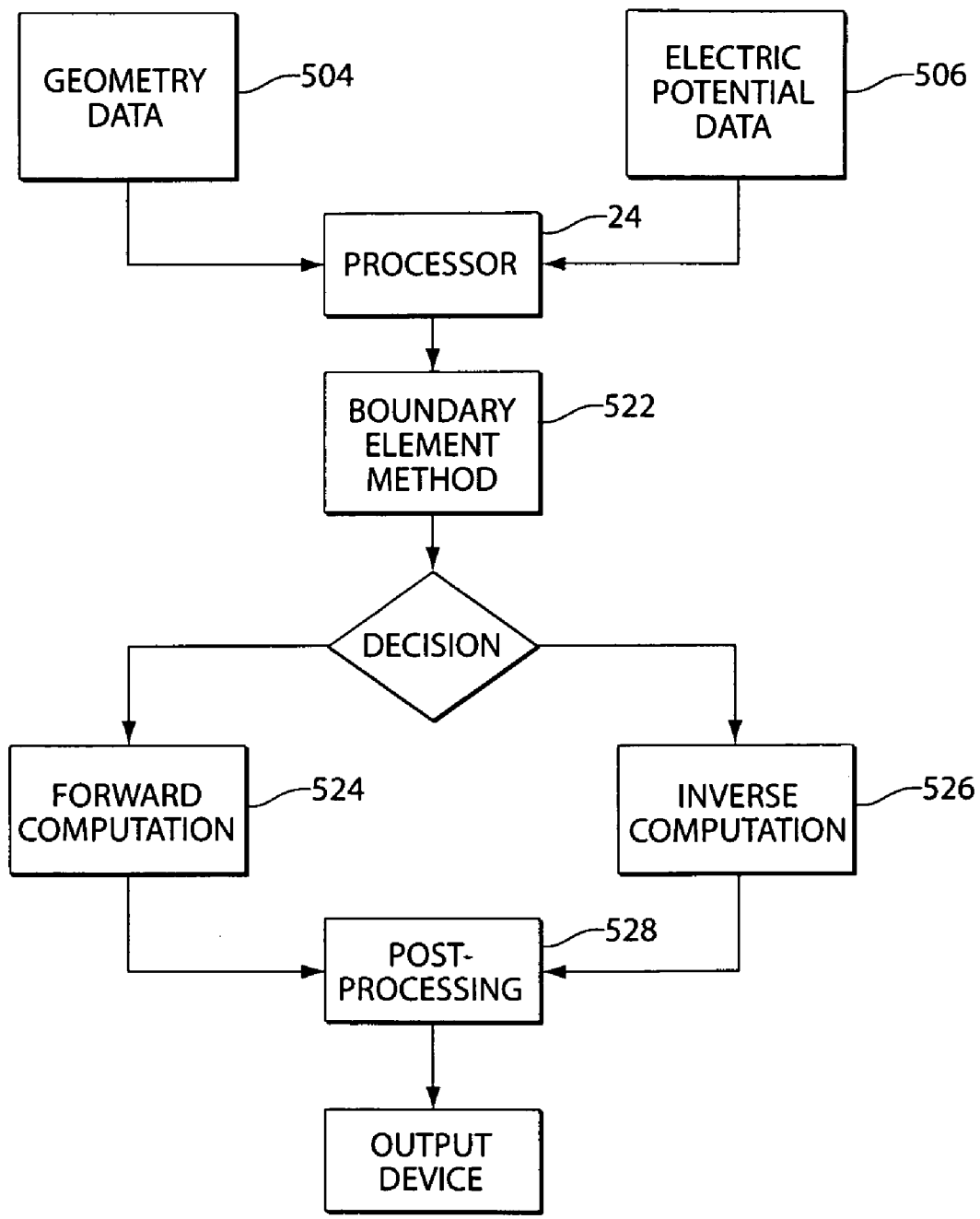
FIG. 5b is another exemplary block diagram for determining epicardial potentials.

Those of ordinary skill will recognize that the modules and/or components of FIG. 5a are merely illustrative for explanatory purposes, and such modules can be otherwise combined and/or dispersed amongst one or more processors. Accordingly, FIG. 5b includes an embodiment according to FIG. 5a where data 504 from a geometry determining device 26 and electrical potential data 506 from a body surface measuring device 12, 14, 16 can provide input 500 to the processor 24. As FIG. 5b indicates, the input data and other data can be conditionally processed and provided to a boundary element module 522. Forward computations 524, or computing torso potentials from known epicardial potentials, and/or inverse 526 computations, or computing epicardial surface potentials based on measured torso potentials, as provided herein, can employ data from the boundary element module 522. Those of ordinary skill will recognize that in clinical applications, inverse computations 526 are computed. Once the forward and/or reverse computations are performed 524, 526, output and/or post-processing 528 can be performed, and optionally, output files can be generated.

Figure 5C:
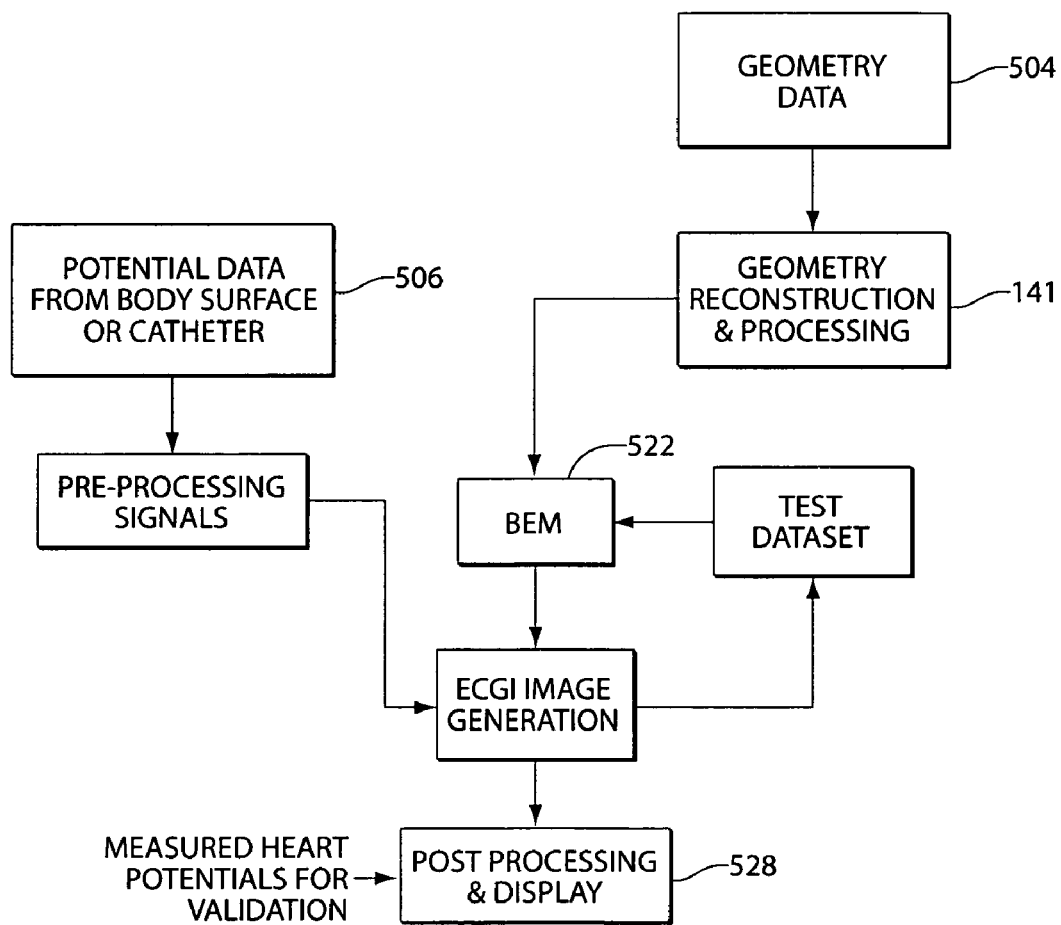
FIG. 5c is another exemplary block diagram for determining epicardial potentials

FIG. 5c provides another exemplary block diagram for determining epicardial potentials.

Figure 6:
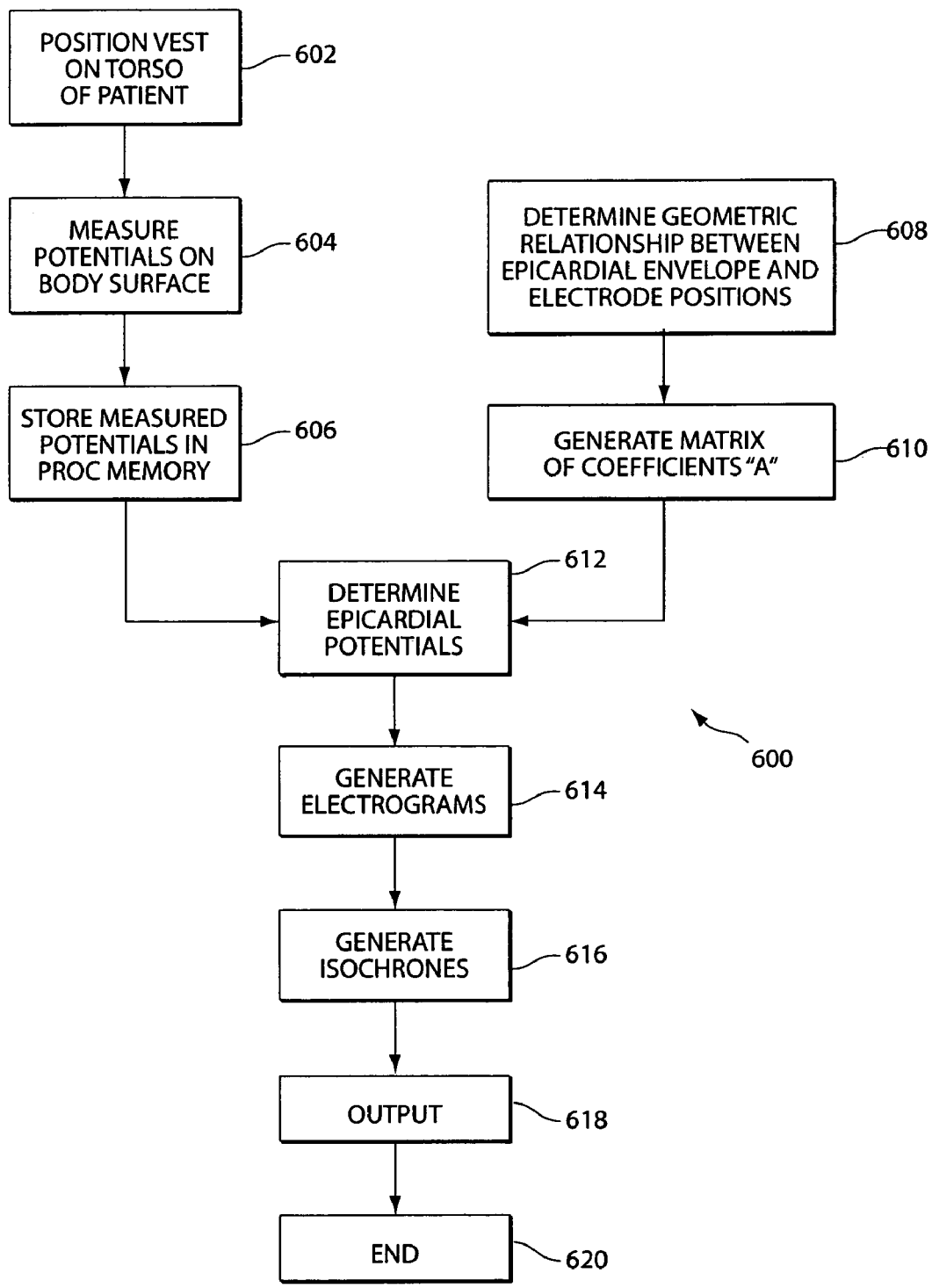
FIG. 6 is an exemplary flow diagram for determining epicardial potentials.

FIG. 6 provides another illustration 600 for one embodiment of the disclosed methods and systems for determining epicardial potentials from geometry determining device data and body surface electrical potential data. In the FIG. 6 example, an electrode vest 12 can be positioned on the torso of a human 602 to provide measurements of electrical potentials of the human's body (torso) surface 604. In the FIG. 6 embodiment, these body surface electrical potentials can be stored in a memory 606. Further, a geometry determining device 26 can be used to provide a geometric relationship between the torso geometry (e.g., electrode positions of the vest) and the human's epicardial envelope, or epicardial surface 608. Based on this geometric relationship between the vest electrodes and epicardial envelope, a matrix of coefficients, A, can be generated 610.

Accordingly, epicardial (surface) potentials, or the electrical potentials on the surface of the heart, can be determined based on the stored body surface potentials and the matrix of coefficients 612 that relates the potentials from the body surface to the epicardial surface. Electrograms and isochrones, for example, and other data representations can be generated 614, 616 based on the epicardial surface potentials, and optionally output 618 to a device 28.

Those of ordinary skill will recognize that computing torso potentials based on measured epicardial potentials (the "Forward Problem") includes solving Laplace's equation which entails the discretization of Laplace's equation (using Green's second theorem as described in, for example, Jackson J D, Classical electrodynamics, John Wiley and Sons, New York (1975)) in the volume between the epicardial surface and the body surface. A known boundary element method (BEM) (e.g., Brebbia C A, Telles J C F, Wrobel L C, Boundary, element techniques. Theory and applications in engineering, Springer Verlag, Berlin (1984) or Brebbia et al., Boundary Elements: An Introductory Course, McGraw-Hill, New York (1989)) can be employed.

Accordingly, a relationship between the epicardial (surface) potentials and the torso potentials can be expressed as the following linear matrix relationship:

$$V_T = A V_E \tag{1}$$

where $V_E$ is the vector of epicardial potentials, $V_T$ is the vector of torso potentials, and A is the $N_T \times N_E$ of transfer matrix of influence coefficients between the heart (or epicardial envelope) and the torso (or electrode positions). The A matrix is thus based on the geometry and the conductivities of the media in the volume between the heart and torso. Although the torso can be understood to be homogeneous (i.e., uniform conductivity between the epicardial surface and the body surface), the A matrix can be modified to account for torso inhomogeneities (e.g., lungs, etc.). Accordingly, Equation (1) represents the forward problem of electrocardiography for computing body surface potentials from epicardial potentials.

One of ordinary skill can thus recognize that the A matrix is based on the geometrical relationship between the epicardial surface or envelope and the torso, and accordingly, the A matrix is based on node positions (corresponding to electrode positions) on the torso and node positions on the epicardium.

Equation (1) can thus also be rearranged to express the epicardial potentials in terms of the body surface potentials and the inverse of the A matrix:

$$V_E = A^{-1} V_T \tag{2}$$

The problem of determining the inverse of the A matrix is ill-posed as small perturbations in the data (e.g., measurement noise or geometrical errors) can cause large unbounded errors, which accordingly can require regularization of the solution to Equation (2). In one embodiment, Tikhonov regularization (See, Tikhonov A N, Arsenin V Y, "Solutions of ill-posed problems," (trans from Russian) Wiley, N.Y. (1977), or Tikhonov et al., "Solutions of ill posed problems," 27–94, V H Winston & Sons, Washington D.C. (1977) which are hereby incorporated herein by reference) can be used to stabilize the solution to Equation (2) by imposing constraints on the magnitudes or derivatives of the computed epicardial potentials, which includes determining an epicardial solution, $V_E$, that minimizes the following objective function:

$$\text{Minimize over } V_E (\|A V_E - V_T\|^2 + t\|L V_E\|^2) \tag{3}$$

The first term in Equation (3) represents the least-square solution of equation (2), while the second term in Equation (3) is a regularization term that imposes bounds on the amplitude of the solution to Equation (2). Those of ordinary skill recognize that the regularization parameter, t, controls the degree of the imposed constraint and provides a balance between the accuracy and stability of the solution, while L is a regularization operator (e.g., unity, gradient, or Laplacian). In one example, the regularization parameter, t, can be determined using the CRESO (Composite Residual and Smoothing Operator) method. (See, for example, Colli Franzone P, Guerri L, Tentoni S, Viganotti C, Baruffi S, Spaggiari S, Taccardi B, "Mathematical procedure for solving the inverse problem of electrocardiography," Math Biosci, 77:353–96 (1985), and Colli-Franzone et al., "Finite element approximation of regularized solutions of the inverse problem of electrocardiography and applications to experimental data" Calcolo, 1985, 22:91–186, which are incorporated herein by reference) and has been found to perform comparably to the "optimal" t that provides the minimum RMS error between the computed $V_E$ and the measured $V_E$ (e.g., experimental studies). See, Messinger Rapport B J, Rudy Y, "Computational issues of importance to the inverse recovery of epicardial potentials in a realistic heart-torso geometry" (published erratum appears in Match Biosci April 1990;99 (1):141], Math Biosci, 97:85–120 (1989), which is incorporated herein by reference. The CRESO regularization parameter, t, depends on the vector $V_T$ and the matrix A. Accordingly, computing the epicardial potentials, $V_E$, is based on non-invasively obtained data that includes the torso surface electric potentials, $V_T$, (e.g., torso vest electrode data) and geometry data (e.g., CT, bi-plane X-ray, etc., to develop the A matrix).

As provided herein, Tikhonov regularization imposes constraints on the magnitudes or derivatives of the computed epicardial potentials to provide a solution. Applying these constraints requires some a-priori knowledge of the solutions' properties, which, in the illustrated embodiments, can cause a spatial smoothing of epicardial potentials that may reduce spatial resolution and diagnostically meaningful data or information. The Tikhonov regularization also requires an accurate determination of the aforementioned regularization parameter, t, which determines the constraint level. The aforementioned methods to determine the regularization parameter (e.g., Composite Residual and Smoothing operator (CRESO), L-curve, and Zero crossing) may not perform consistently and can be sensitive to the noise-level of the data. In some cases, a-priori information and manual adjustment may be required to choose an optimal regularization parameter. For example, a-priori knowledge of the number of ectopic foci (sites from which excitation is initiated) may influence the level of regularization applied.

A complementary approach to solving Equation (2) includes the Generalized Minimal Residual (GMRes) method which, unlike the Tikhonov regularization, is not based on imposing constraints and therefore does not include a-priori data or information about the solution or determination of a regularization parameter. Referring again to Equation (2), GMRes is thus an iterative method of computing $V_E$ from $V_T$ without imposing constraints on the solution.

As in known in the art, the GMRes method belongs to the class of Krylov subspace iterative methods. Generally, for the linear problem Ax=b, where A is a matrix and x is a vector (see, e.g., Equation (1)), the Krylov space of A is the subspace spanned by x, Ax, $A^2x$, etc. Accordingly, if M is a preconditioner, such that $M^{-1}A \approx I$ (identity matrix), then for $M^{-1}(Ax-b) \approx e$, as e approaches zero, $M^{-1}$ approaches an approximation of $A^{-1}$. Hence, an iteration can be constructed as $x^{k+1} = x^k + M^{-1}(Ax^k - b)$, where the error at an iteration k can be expressed as $M^{-1}(Ax^k - b)$. Those of ordinary skill will recognize that GMRes is one approach for reducing the error to provide an approximation for $M^{-1}$ (i.e., $A^{-1}$) which uses an orthogonal Arnoldi decomposition of the A matrix.

Accordingly, with specific reference to Equations (1) and (2), given a vector $V_T$ and the matrix A, an n-dimensional Krylov subspace K(n) can be based on a set of linear combinations of the vectors $V_T, AV_T, A^2V_T, \ldots, A^{n-1}V_T$.

At the $n^{th}$ GMRes iteration, the A matrix inverse can be approximated by a projection of A, $p_n(A)$, onto K(n). Accordingly, based on Equation (2), epicardial potentials, $V_E$, can be approximated by $p_n(A)V_T$.

The GMRes method proceeds by constructing, at the nth iteration, an orthonormal basis for the Krylov sub space, K(n). Because the A matrix is generally non-square (e.g., number of torso electrodes is generally not equal to number of reconstruction points on the epicardium), the disclosed methods and systems can be understood to include multiplying both sides of Equation (1) by $V_T$ and applying a GMRes method to the solution of $A^T AV_E = A^T V_T (A^T A$ is a square matrix). Since the Krylov subspaces form a nested sequence, the norm of the residual error, $\|AV_E - V_T\|$, decreases as n increases. A solution with reduced contamination from noise components can be achieved by stopping the iterations of the GMRes method.

As provided herein, at the $n^{th}$ GMRes iteration, the matrix $A^{-1}$ can be approximated by the projection of A, p(A), onto the Krylov subspace, K(n). It is understood in the art that such projection subspace, K(n), can be represented as an upper triangular Hessenberg matrix, H(n). Further, the number of iterations (e.g., the value of n) can be based on the observation that, as n increases, the condition number of H(n) increases (i.e., H(n) can become ill-conditioned) while the norm of the residual error, $\|AV_E - V_T\|$, decreases. A plot of the condition number of H(n) versus the norm of the nth residual error illustrates the effect of GMRes iterations on these two quantities, and is shown as FIG. 7.

Figure 7:
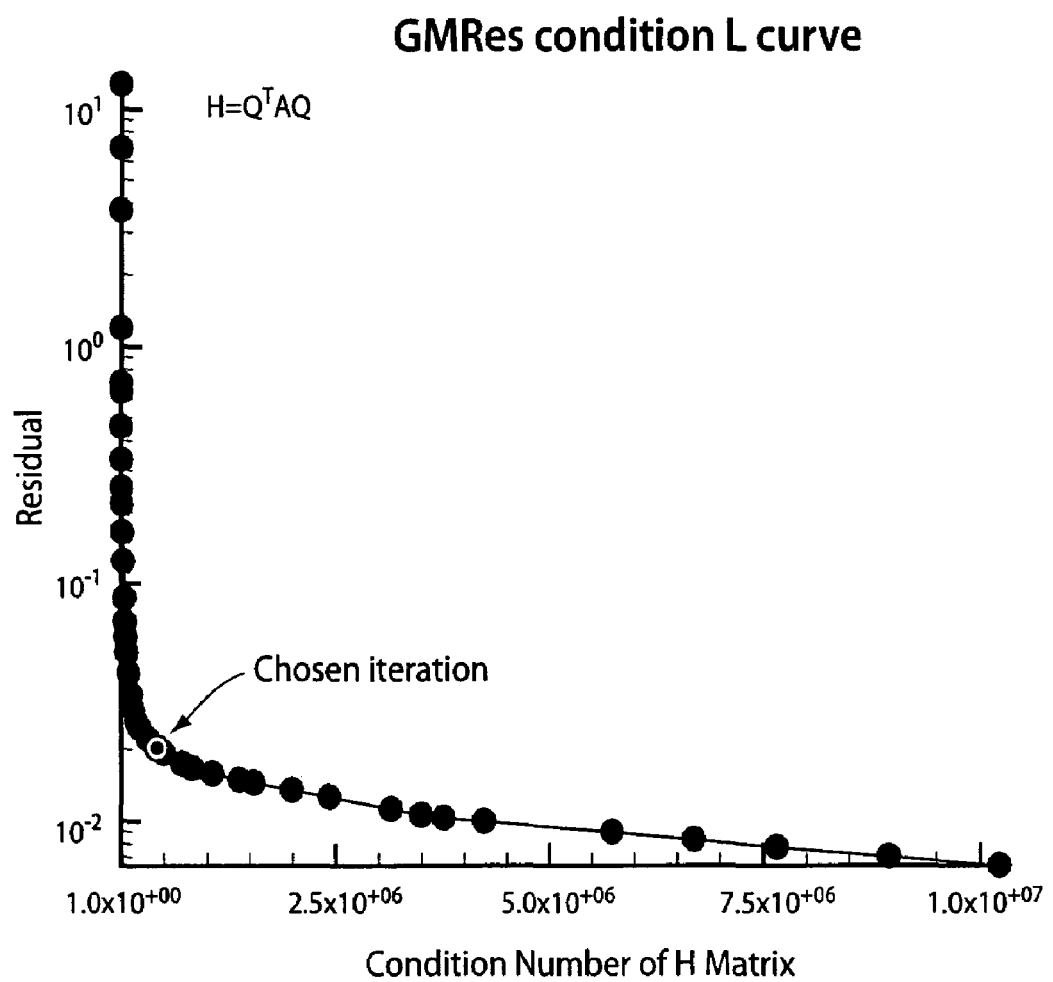
FIG. 7 represents a condition L curve.

As FIG. 7 indicates, for a method and system that utilize GMRes to compute a solution to Equation (2) and hence can be based on a number of iterations, as the iteration number increases, the condition of an associated Hessenberg matrix can be accompanied by a decrease in the norm of the residual error, $\|AV_E - V_T\|$. As FIG. 7 indicates, this decrease can be comparatively significant during the first iterations when compared to subsequent iterations. Accordingly, one of skill in the art will recognize that the incremental decrease in residual error, $\|AV_E - V_T\|$, for additional iterations, may be insignificant after a given number of iterations, while the condition number of the Hessenberg matrix continues to increase.

Based on FIG. 7, one compromise between number of iterations, decreased residual error, and Hessenberg matrix condition can include selecting a number of iterations for the GMRes method that is associated with or otherwise based upon a representation of residual error versus condition number, and where such number of iterations can be a compromise between residual error decrease and condition number increase. For the FIG. 7 embodiment, for example, a selected or chosen number of iterations can be associated with the "elbow" of a curve that represents residual error (norm) based on condition number of the Hessenberg matrix. Those of ordinary skill will recognize FIG. 7 to represent a "condition L curve," which has a corner that can otherwise be understood to be an elbow. In one embodiment, a corner of a condition L curve can be selected by a curvature detection module that computes curvature along a condition L curve. In one example, a selected number of iterations can be a number of iterations associated with a comparative maximum curvature of a condition L curve. In an embodiment, a selected number of iterations can be determined from a corner of a "L curve" (compare to "condition L curve") that can plot or otherwise represent residual error (norm) and (e.g., versus) solution norm. Accordingly, in such an embodiment, a number of iterations can be based on the corner of a L curve, which can be based on a comparative maximum curvature, although other methods can be used.

In some embodiments, a selected number of GMRes iterations can be determined based on an increase in spatial frequency of a reconstructed potential map, where such evaluation can be performed after an iteration of the GMRes technique, and can be based on a Fourier transform or other frequency representation of a potential map. Further, a selected number of GMRes iterations can be based on comparative amplitudes of a solution norm that is computed at an iteration, where a comparatively increased amplitude in a solution norm at a selected iteration can be a basis for selecting an iteration number. The aforementioned four techniques for selecting a GMRes iteration number are shown in FIG. 8 818, and those of ordinary skill in the art will recognize that other techniques can be used.

Figure 8:
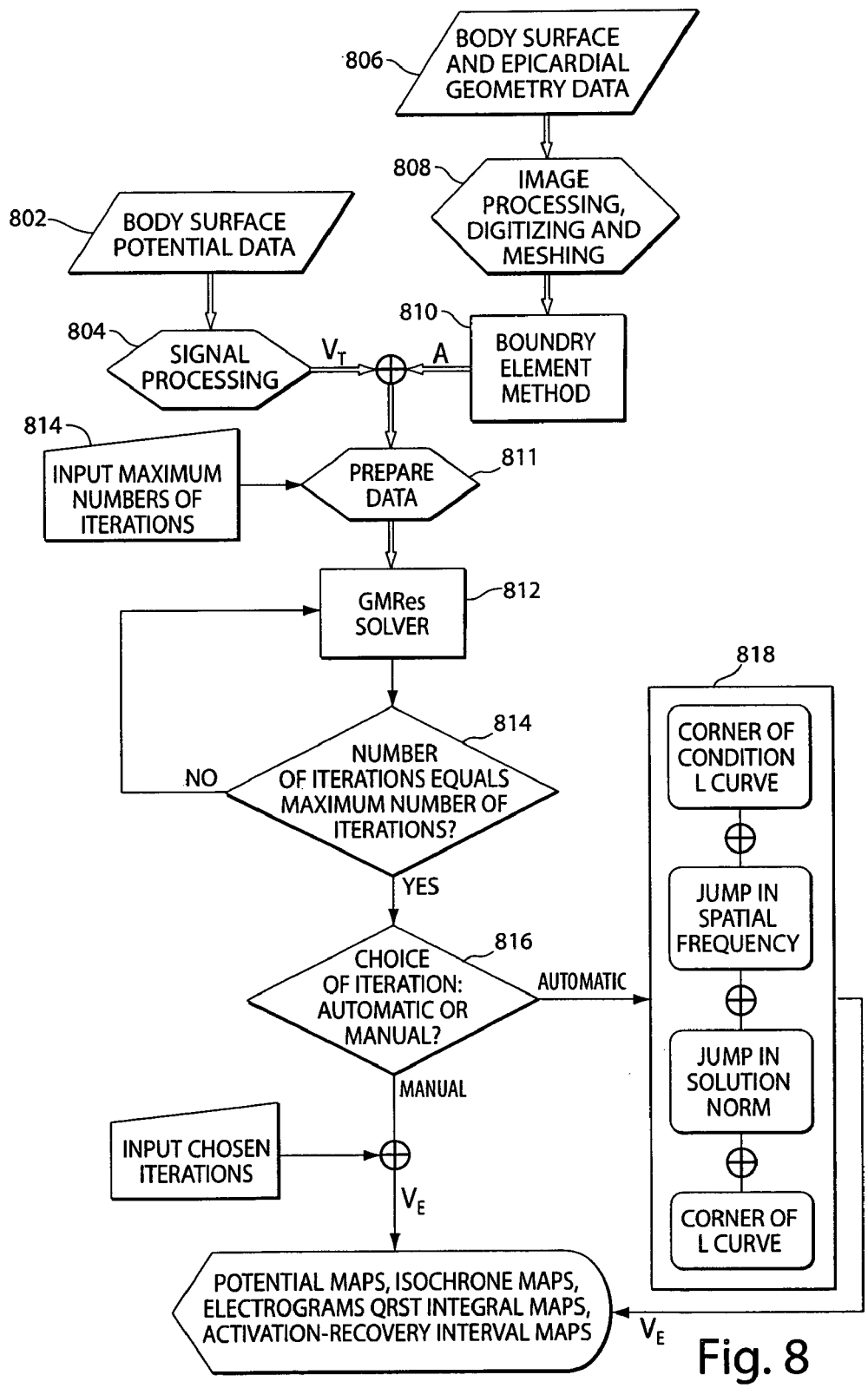
FIG. 8 is a block diagram for determining epicardial potentials using a GMRes module.
Figure 9A:
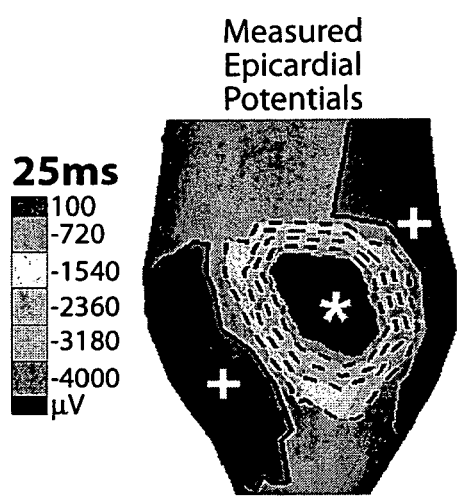
FIGS. 9a, 9b, and 9c present epicardial potential maps for pacing from a single anterior ventricular site, 25 milliseconds after a pacing stimulus, as measured, and as reconstructed using GMRes and Tikhonov reconstructions, respectively.
Figure 9B:
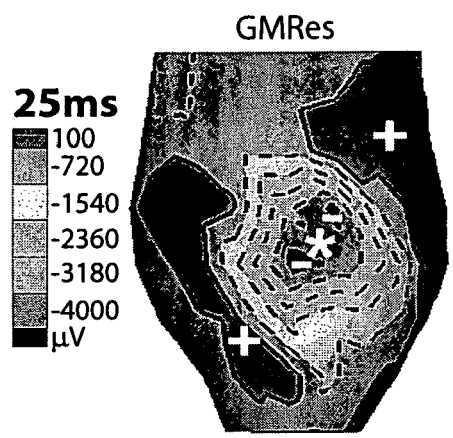
Figure 9C:
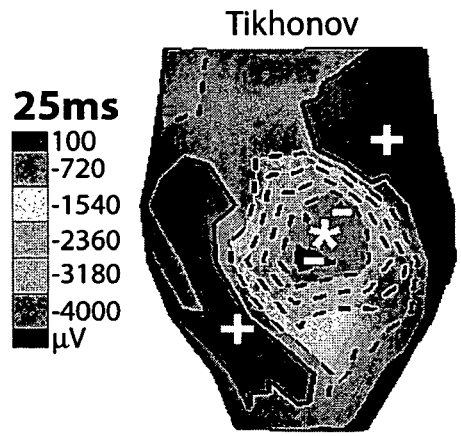
Figure 9D:
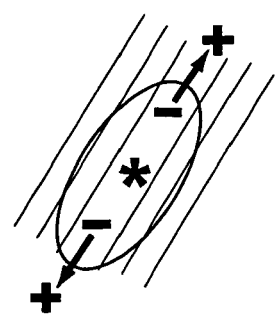
FIG. 9d shows an equivalent dipole source and theoretical potential pattern associated with single-site pacing.

FIG. 8 presents one illustrative block diagram for the disclosed systems and methods that employs a GMRes module to compute epicardial surface electric potentials based on body surface electrical potential data and geometrical relationships between the body surface and the epicardial surface. As FIG. 8 indicates, body surface electric potential data 802 can be provided by a vest 12 or other body surface device for measuring electric potentials (e.g., ECG/EKG, etc.), where such data can be input to a signal processing module 804 to determine a vector of body surface electric potentials, $V_T$. Further, a geometry determining device 24 such as a CT scan, MRI, bi-plane or single plane x-ray fluoroscopy, and other known techniques, can provide body surface data (e.g., vest electrode positions, etc.) and epicardial geometry data 806 which can be processed by an image processing module 808 and/or boundary element method module 810 to produce a transfer matrix, A, representing the geometric relationships between the body surface and epicardial surface. The A matrix and $V_T$ data can be prepared 811 for input to a GMRes module 812. Another input to the GMRes module 812 can be a maximum number of iterations 814. As provided herein, the GMRes module 812 can be repeated for a number of iterations 814 that can be equal to the maximum number of iterations 814, whereupon residual error and Hessenberg matrix data can be provided for the various iterations, including for example, other data based on the condition of the Hessenberg matrix at an iteration. Based on whether the FIG. 8 embodiment employs an automatic and/or a manual computation 816 of a GMRes number of iterations for approximating the A matrix inverse, data from the GMRes module can be used to determine an approximation for the A matrix inverse, and accordingly, at least one vector of epicardial surface potentials, $V_E$, can be computed or otherwise determined.

Based on a system and method according to FIG. 8, if a manual computation of a number of iterations for approximating the A matrix inverse is selected 816, data from the GMRes module 812 corresponding to the number of iterations can be employed to compute an approximation of the A matrix inverse, whereupon epicardial surface potentials, $V_E$, can also be computed based on the approximation and the body surface electric potentials, $V_T$. Also, if an automatic number of iterations is selected or otherwise designated 816, an iteration module 818 can be employed to determine a number of iterations upon which an approximation of the A matrix inverse can be computed (i.e., based on corresponding data from the GMRes module 812), and epicardial surface potentials, $V_E$, can be computed based on the approximation and the body surface electric potentials, $V_T$.

As indicated by the illustrative iteration module 818, one or more techniques can be used to determine a number of iterations from which to base the approximation of the A matrix inverse, where such techniques were previously described herein. Such "automatic" determination can be based on the GMRes module data, where, as provided herein, a plot or other comparison of residual error and Hessenberg matrix condition can be computed to determine a corner of a condition L curve. One or more of the illustrated techniques 818 and other methods can be used and compared, for example, to provide an iteration number. Data associated with the iteration number (e.g., Hessenberg matrix, etc.) can be retrieved from the GMRes module 812 or other location to compute an approximation to the A matrix inverse. Several experiments were conducted using isolated canine hearts in a human-shaped torso tank, where a Langendorff perfused dog heart was suspended in an approximate anatomic position in a human-shaped torso tank to facilitate simultaneous recording of body surface and epicardial potentials for single and dual pacing from various sites.

For the single pacing embodiment, body surface and epicardial potentials were simultaneously recorded during pacing from a single anterior epicardial site to provide a data set for simulating an arrhythmogenic ectopic focus and providing data for evaluating the aforementioned GMRes systems and methods for localizing initiation sites of arrhythmic activity and other comparatively highly localized electrophysiological events.

For the dual pacing embodiment, epicardial potentials were recorded for simultaneous pacing from pacing sites distanced by 2.5 centimeters. The recorded potentials were used to compute body-surface potentials in a computer model of the human torso that included the thoracic inhomogeneities of lungs, muscle, bone, and fluid layers. The computed body surface potentials were used to reconstruct epicardial potentials in a homogeneous torso of the same geometry. The dual pacing data set allowed an evaluation of the reconstruction accuracy of GMRes while assuming a homogeneous torso (an approximation that greatly simplifies the clinical application of ECGI), and an evaluation of the accuracy and spatial resolution of GMRes in localizing two closely-spaced pacing sites.

Additionally, open chest canine experiments were performed by measuring epicardial potentials from hearts of open chest dogs (i.e., exposed by sternotomy) using a multi-electrode epicardial sock. The open chest data was used to compute body surface potentials in a homogeneous or inhomogeneous computer model of the human torso. Measurement noise (e.g., 50 $\mu$V peak-to-peak, Gaussian) and geometrical errors (e.g., 1 mm, Gaussian) were added to the body surface potentials and electrode positions, respectively, to simulate experimental or clinical measurements. These "contaminated" body surface potentials were then used to reconstruct epicardial potentials using the ECGI methodology.

Epicardial potentials during right atrial pacing (i.e., simulating normal sinus rhythm) were recorded from a 490-electrode sock. A region of infarcted tissue was created by the ligation of the left anterior descending coronary artery (LAD) and ethanol injection. This data set allowed an evaluation of the GMRes methods and systems to reconstruct abnormal electrophysiological properties of an infarct substrate.

Infarction was produced in a canine heart through ligation of the LAD. After four days of infarct formation in a closed chest, the chest was opened again and a 490-electrode sock pulled over the heart to record potentials. Monomorphic Ventricular Tachycardia (VT) due to double-loop epicardial reentry was induced through programmed stimulation and recorded. This data set was used to evaluate the GMRes methods and systems for reconstructing the reentry pathway and its various electrophysiological components.

Abnormal and heterogeneous repolarization is understood to be an underlying mechanism of many arrhythmias. Localized epicardial cooling was applied to prolong action potential duration in a region of the LV and consequently increase dispersion of repolarization. Epicardial potentials were recorded during RA pacing and QRST integral maps were computed to reflect local repolarization properties.

For the data sets presented herein, epicardial potentials were reconstructed using the GMRes method and the results were validated by direct comparison to measured epicardial potentials, which served as the gold standard. A zero initial value was used as a starting point for the GMRes iterations. The GMRes results were also compared with corresponding Tikhonov reconstructions. A hybrid method (Tik-GMRes method) was also developed and evaluated. In the hybrid method, GMRes solutions were computed with the Tikhonov solution (rather than zero) as the starting point for the iterative scheme.

Epicardial potential maps were reconstructed which depict the spatial distributions of potentials on an epicardial envelope of the heart. Although an epicardial potential map depicts one instant of time, epicardial potential maps were computed at intervals of one millisecond during an entire cardiac cycle. Electrograms were also reconstructed depicting the variation of potential with respect to time at a single point on the epicardium. The reconstructed electrograms were generally computed at approximately two-hundred to five-hundred sites or points around the epicardial envelope. Further, isochrone maps were reconstructed which depict the sequence of epicardial activation based on local activation time taken as the point of maximum negative derivative (–dV/dtmax) of each electrogram.

Results were based on visual comparison and, when possible, included statistical measures in the form of relative errors and correlation coefficients.

FIG. 9 shows epicardial potential maps for pacing from a single anterior ventricular site (indicated by asterisk), 25 milliseconds after a pacing stimulus. FIG. 9a presents directly measured epicardial potentials, with the corresponding GMRes and Tikhonov reconstructions shown in FIGS. 9b and 9c, respectively. The measured potentials display a central negative region containing a minimum at the pacing site (asterisk), flanked by two positive regions containing local maxima (+). FIG. 9D is adapted from Oster et al. (Oster H S, Taccardi B, Lux R L, Ershler P R, Rudy Y., "Noninvasive electrocardiographic imaging: reconstruction of epicardial potentials, electrograms, and isochrones and localization of single and multiple electrocardiac events," Circulation. 1997;96:1012–1024.) which shows an equivalent dipole source and theoretical potential pattern associated with single-site pacing. The illustrated pacing site is surrounded by a negative region which contains two potential minima (–). Two corresponding potential maxima (+) are present in the flanking positive region. The entire pattern is oriented along the axis of myocardial fibers (background lines) in this region. The reconstructed GMRes and Tikhonov maps (FIGS. 9b and 9c) capture the two minima in the central negative region. Note that the measured map, FIG. 9a, shows only one central minimum because of limited spatial resolution (insufficient density of measuring electrodes). The GMRes reconstruction is comparable in accuracy to the Tikhonov reconstruction, with both locating the pacing site to within three millimeters of the actual position, while both correctly reproduce the progression of potential patterns during the entire paced beat (only 25 milliseconds is shown). Similar accuracy was obtained for potential maps generated by left-lateral and postero-lateral pacing (not shown).

FIG. 10 shows epicardial potentials generated by simultaneous pacing from two closely spaced sites (e.g., 2.5 cm apart), indicated by asterisks. FIG. 10a shows potential maps during activation, or 25 ms after the pacing stimulus. Body surface potential maps (BSPM) shown in FIG. 10a(1) were the input data for the noninvasive GMRes and Tikhonov reconstructions. FIG. 10a(2) shows measured epicardial potentials with two potential minima at each of the two pacing sites. It is noted that the corresponding BSPM shows one minimum without an indication of dual pacing. From the smoothed BSPM data, the GMRes method provided reconstruction of two pacing sites with reasonable localization accuracy, with the left minimum within four millimeters, and right minimum within six millimeters of the corresponding pacing sites (FIG. 10a(3)). The Tikhonov method (FIG. 10a(4)) allows reconstruction of one elongated minimum, which suggests more than one pacing site, yet this method fails to capture or otherwise detect two distinct minima. It is noted that a smoothing property of such constrained regularization can cause a loss of spatial resolution.

Figures 1, 10A:
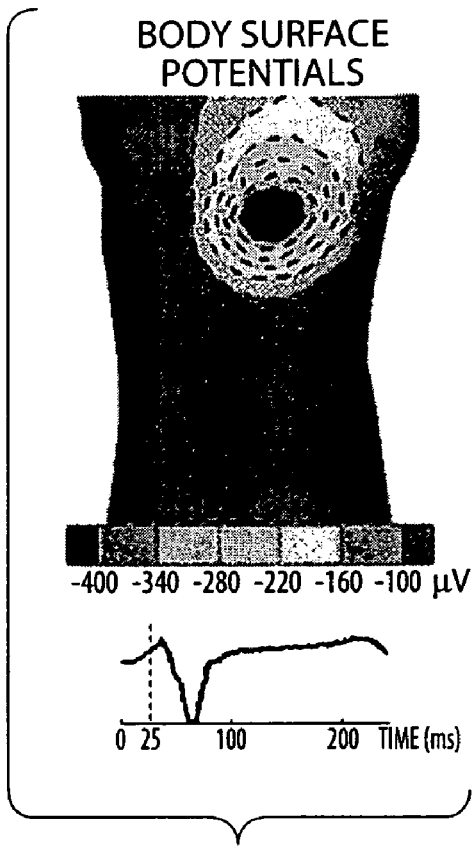
FIGS. 10a and 10b present epicardial potentials generated by simultaneous pacing from two closely spaced sites (e.g., 2.5 cm apart), during activation and repolarization, respectively.
Figures 2, 10A:
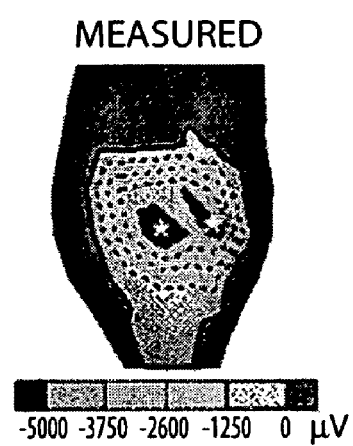
Figures 3, 10A:
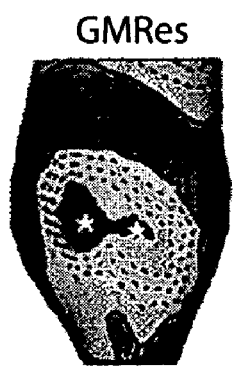
Figures 4, 10A:
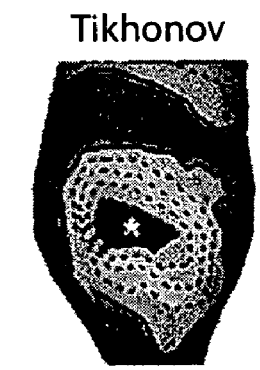
Figures 1, 2, 10B:
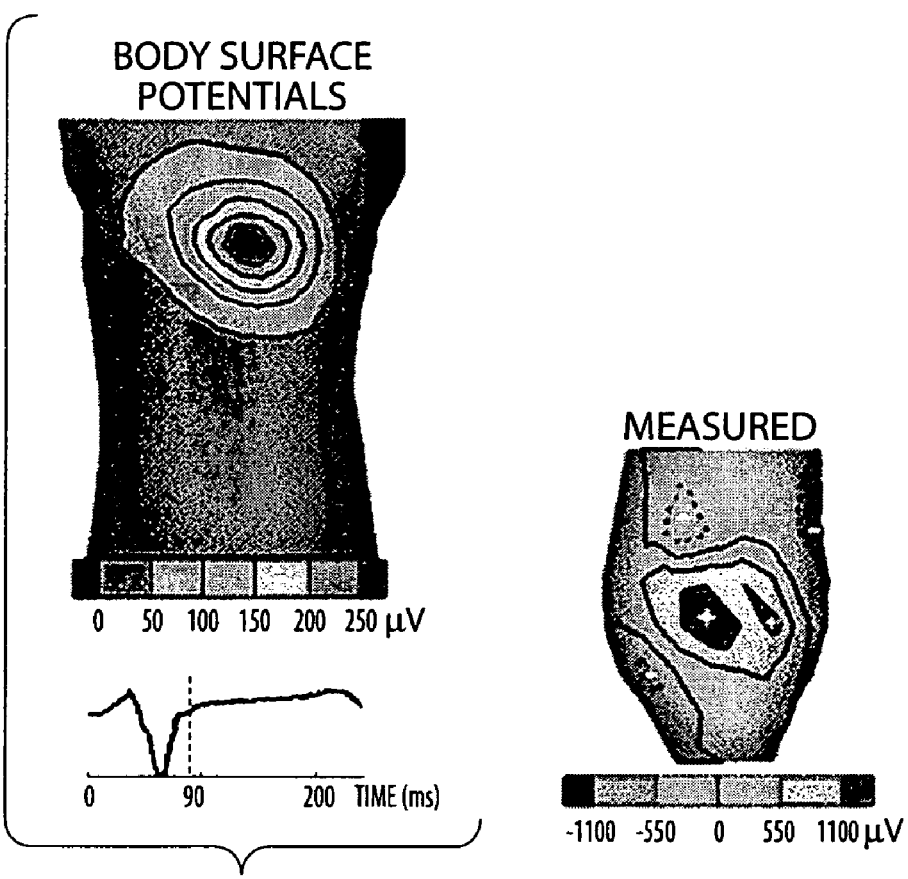
Figures 3, 4, 10B:
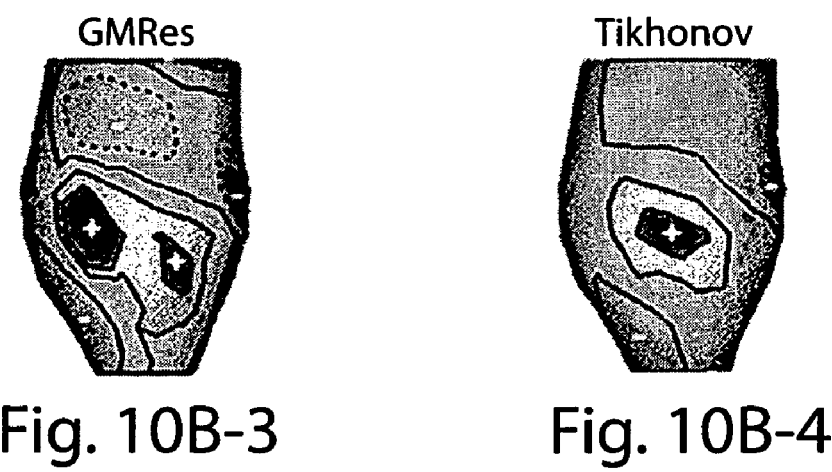

FIG. 10b shows potential maps during repolarization, or 90 milliseconds after the pacing stimulus. The repolarization pattern is similar to the activation pattern, except that the polarity is reversed. Accordingly, two maxima, indicated by +, correspond to the minima at the pacing site locations for the activation pattern. Referring to FIG. 10b(1), one maximum is present in the BSPM, while in FIG. 10b(3), the GMRes reconstructed repolarization pattern includes two maxima. The Tikhonov method reconstruction, shown in FIG. 10b(4), includes one elongated maximum.

Based on FIG. 10, in certain embodiments, a method and system that employs GMRes can resolve multiple electrophysiological events (e.g., initial activation sites) with higher spatial resolution than a constraint-based Tikhonov approach.

Figure 11A:
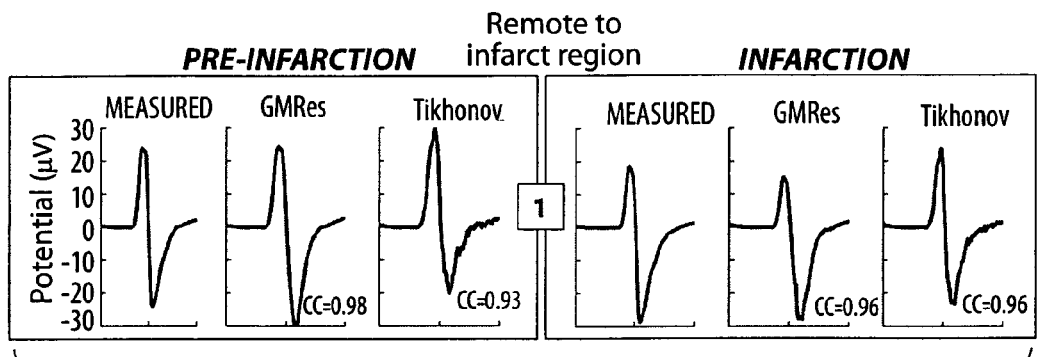
FIGS. 11a, 11b, and 11c present electrograms from a first site on the right ventricle, and second and third sites in the left ventricle, respectively.
Figure 11B:
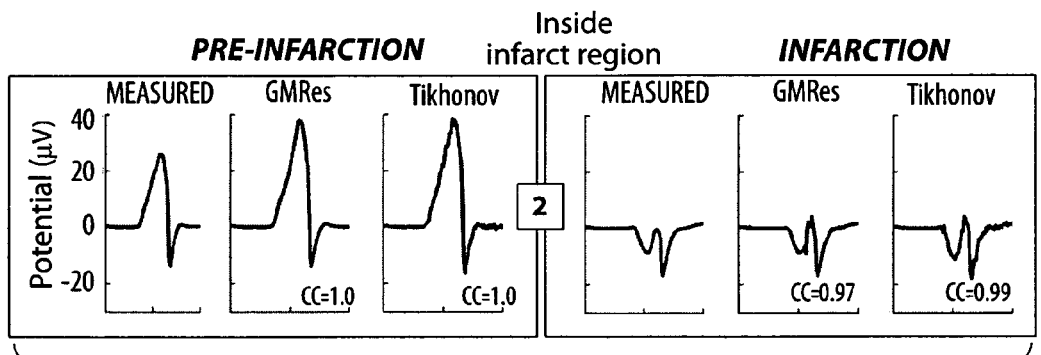
Figure 11C:
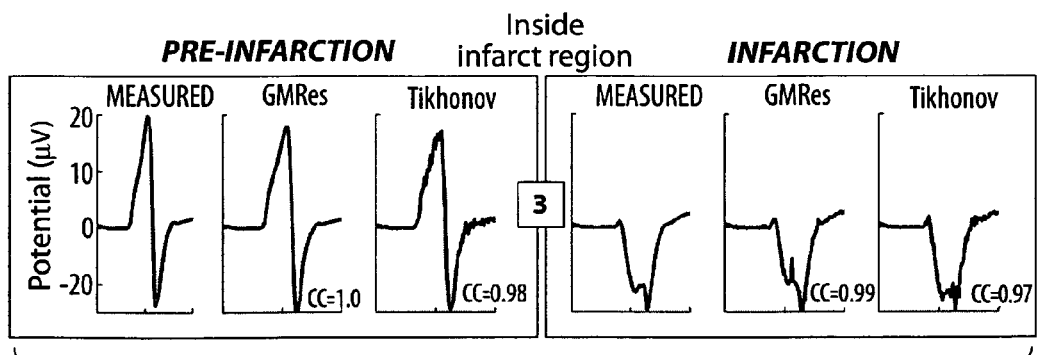

FIG. 11 shows epicardial electrograms pre-infarction and post-infarction. FIG. 11a shows electrograms from a first site located on the right ventricle, remote to the LV infarct location. Panel A shows electrograms from the control heart (pre-infarction), with directly measured electrograms and corresponding GMRes and Tikhonov (Tik) reconstructions. Electrograms from the infarcted heart from the same location are shown in panel B. The measured electrograms pre-infarction and post-infarction show normal RS morphology with a sharp intrinsic deflection indicating local activation (i.e., electrograms at this location are not affected by the remote infarct and maintain their pre-infarction morphology). Both GMRes and Tikhonov reconstructions show similarity to the measured electrograms. FIGS. 11b and 11c show electrograms from second and third sites, respectively, in the LV inside the infarct region. Panel C shows pre-infarction electrograms and panel D post-infarction electrograms. Pre-infarction electrograms from the second and third sites show typical RS morphology similar to the first site; however, the infarct produces a change in their morphology from RS waves (panel C) to negative slow Q waves (panel D). The Q waves contain superimposed sharp small deflections that likely indicate local activation of islands of surviving myocardium within the infarct. The GMRes reconstructions and Tikhonov reconstructions show similarity to the directly measured electrograms and capture the infarction-induced changes, including the smaller deflections generated by surviving myocardium. The Tikhonov electrograms are "jagged" in appearance due to the variation in regularization parameter from time-frame to time-frame. The corresponding GMRes electrograms are smoother, without sacrificing detail in the measured electrograms.

FIG. 12 shows isochrone maps for two cycles of monomorphic ventricular tachycardia (VT). FIGS. 12a and 12b show isochrones constructed from activation times determined from directly measured electrograms. The VT is caused by double loop reentry (black arrows) with a central common pathway in the infarct region between two lines of conduction block (thick black lines). FIGS. 12c, 12d and FIGS. 12e, 12f show corresponding GMRes and Tikhonov reconstructions, respectively. The reconstructions capture the features of the reentrant circuit, showing correlation with the measured isochrones for the two displayed cycles. For similar accuracy, however, the GMRes reconstruction included about half as much manual editing of activation times as the corresponding Tikhonov reconstruction. Actual numbers of edited activation times are shown on the bottom right side of each reconstructed map.

Figure 13:
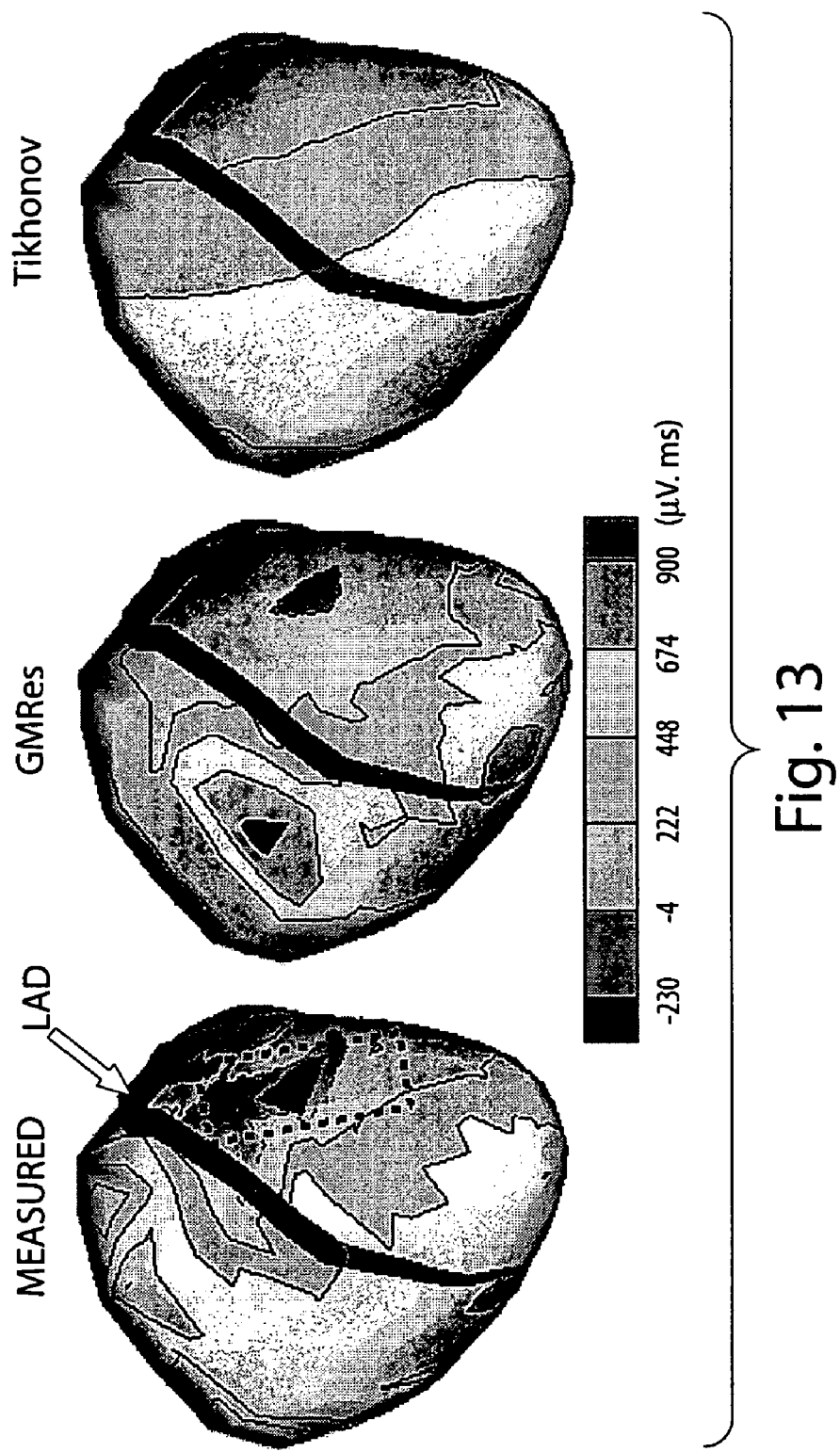
FIG. 13 presents directly measured, GMRes reconstructed, and Tikhonov reconstructed QRST integral maps during local LV cooling; and, FIGS. 14a and 14b show a measured potential map and a corresponding Tikhonov-GMRes hybrid reconstruction, respectively.

FIG. 13 presents directly measured, GMRes reconstructed, and Tikhonov reconstructed epicardial QRST integral maps during local LV cooling. The cooling probe position is shown by the dotted rectangle of the measured map. The measured QRST integral map shows lower QRST amplitudes in the region of cooling with a localized minimum directly under the cooling probe. Although the GMRes and Tikhonov reconstructions show the cooling-induced reduction in QRST integral values similar to the measured map, the GMRes reconstructs the localized minimum under the cooling probe, while the Tikhonov does not. The Tikhonov reconstruction is smoothed, resulting in loss of spatial resolution and under-representation of local repolarization heterogeneities.

Figure 14A:
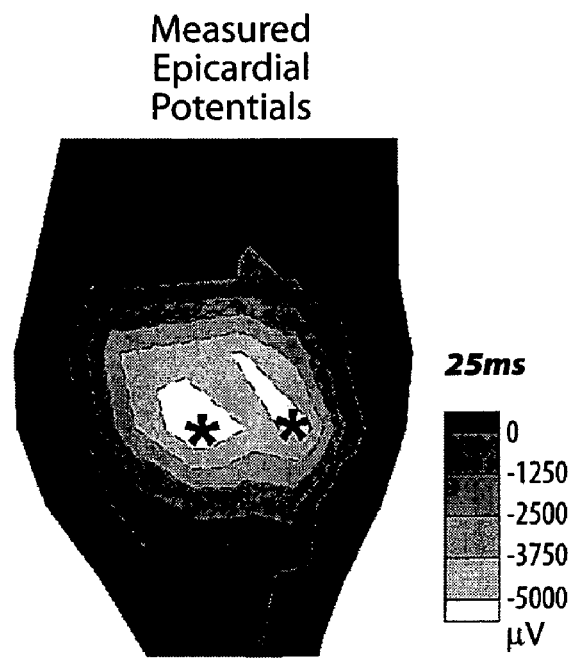
Figure 14B:
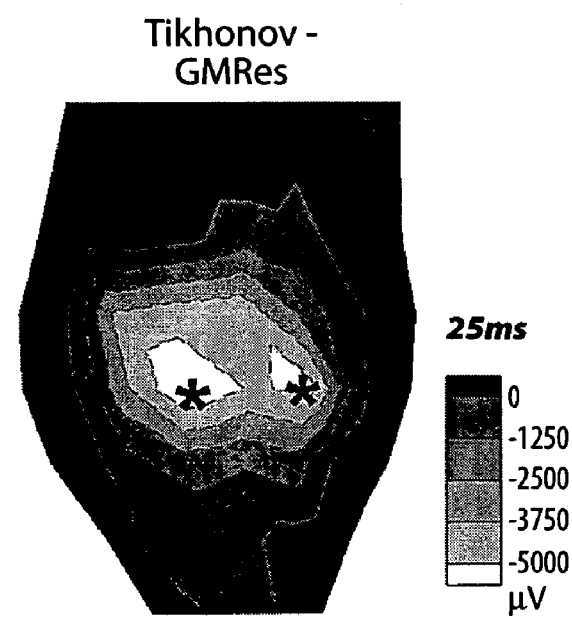

FIG. 14 shows reconstructions using the Tikhonov-GMRes hybrid method applied to the simultaneous dual pacing data of FIG. 10. FIG. 14a shows a measured potential map for a time-frame of 25 milliseconds after the pacing stimulus, while FIG. 14b provides a corresponding Tikhonov-GMRes hybrid reconstruction. FIG. 14b indicates a closer correlation with the pattern of the measured map when compared to the independent application of the GMRes or Tikhonov methods (see FIG. 10). The hybrid method also more accurately locates (e.g., within 1 millimeter) the pacing sites when compared to the independent application of GMRes or Tikhonov methods (see again, FIG. 10).

The sensitivity of the GMRes method to potential noise and geometry errors was also evaluated using the data set of FIG. 9. Various combinations of potential noise (either 50 microvolt or 100 microvolt, Gaussian) and geometrical errors in torso-electrode positions (either one, two, or three millimeter, Gaussian) were added to the input data. The quality of the GMRes solution was comparable to the solution obtained with original data without the added noise.

Further, the hybrid method, which included starting with the Tikhonov solution rather than an initial value of "zero" for GMRes, improved the patterns and localization accuracy of the reconstruction of two pacing sites (FIG. 14). For other data sets, some improvement in accuracy was observed when using the hybrid method.

What has thus been described are methods and systems for computing epicardial surface electric potentials based on measured body surface electric potentials, where the methods and systems include representing at least one geometric relationship between at least one body surface electric potential measuring system and the epicardial surface as a multidimensional matrix, estimating an inverse of the multidimensional matrix based on a Generalized Minimum Residual (GMRes) method, and, based on the inverse matrix and the measured body surface potentials, determining the epicardial surface electric potentials.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) is preferably implemented using one or more high level procedural or object-oriented programming languages to communicate with a computer system; however, the program(s) can be implemented in assembly or machine language, if desired. The language can be compiled or interpreted.

As provided herein, the processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a processor" or "the processor" can be understood to include one or more processors that can communicate in a stand-alone and/or a distributed environment(s), and can thus can be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application.

Although the methods and systems have been described relative to a specific embodiment thereof, they are not so limited. Obviously many modifications and variations may become apparent in light of the above teachings. For example, although the methods and system can be applied to cardiac applications, those of ordinary skill will recognize that other anatomical parts can be imaged accordingly. Further, although the reconstructed data was employed to generate images, electrograms, and isochrones, other data representations can be employed.

Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A method for computing epicardial surface electric potentials based on measured body surface electric potentials, the method comprising:
   representing at least one geometric relationship between at least one body surface electric potential measuring system and the epicardial surface, as a multidimensional matrix,
   using a Generalized Minimum Residual (GMRes) method to estimate an inverse of the multidimensional matrix, and,
   based on the inverse matrix and the measured body surface potentials, determining the epicardial surface electric potentials.

2. A method according to claim 1, where representing includes measuring the position of the at least one body surface electric potential measuring system.

3. A method according to claim 1, where representing includes measuring the position of at least one electrode.

4. A method according to claim 1, where representing includes providing at least one of a CT scan, a MRI and an X-ray.

5. A method according to claim 1, where representing includes determining an epicardial envelope.

6. A method according to claim 1, where representing includes employing a boundary element method.

7. A method according to claim 1, where using a GMRes method includes determining a number of iterations for the GMRes method.

8. A method according to claim 7, where determining a number of iterations includes comparing residual error to a Hessenberg matrix condition, and computing at least one of a corner of a condition L curve and a maximum curvature of a condition L curve.

9. A method according to claim 7, where determining a number of iterations includes determining a number of iterations based on at least one of: a corner of a condition L curve, a corner of an L curve, an increase in spatial frequency of a reconstructed potential map, and an increase in amplitude of a solution norm.

10. A method according to claim 1, where using a GMRes method includes providing a maximum number of iterations for the GMRes method, and based on the data from the maximum number of iterations, determining a number of iterations for the GMRes method.

11. A method according to claim 1, where using a GMRes method includes providing an initial condition of zero.

12. A method according to claim 1, where using a GMRes method includes providing an initial condition based on a Tikhonov regularization of the multidimensional matrix.

13. A method for computing electric potentials on an epicardial surface of a patient, the method comprising:
   measuring electric potentials on the patient's body surface,
   expressing a geometrical relationship between the patient's body surface and the epicardial surface as a multi-dimensional matrix,
   determining an approximation of the two-dimensional matrix based on a Generalized Minimum Residual (GMRes) method, and,
   computing the electric potentials on the epicardial surface based on the approximated inverse and the measured electric potentials.

14. A method according to claim 13, where measuring electric potentials includes measuring electric potentials using a torso vest, where the torso vest includes electrodes.

15. A method according to claim 13, where measuring electric potentials includes measuring electric potentials using at least one electrode.

16. A method according to claim 13, where expressing a geometric relationship includes measuring a location of at least one electrode, where the at least one electrode provides electric potential measurements of the patient's body surface.

17. A method according to claim 13, where expressing a geometric relationship includes measuring a location of the patient's epicardial envelope.

18. A method according to claim 13, where expressing a geometric relationship includes employing a boundary element method.

19. A method according to claim 13, where expressing a geometric relationship includes obtaining data associated with the patient, the data including at least one of CT scan data, MRI data, and X-ray data.

20. A method according to claim 13, where determining an approximation includes providing an initial condition based on at least one of: a zero value and a Tikhonov regularization of the multi-dimensional matrix.

21. A method according to claim 13, where determining an approximation includes determining a number of iterations based on a residual error and a Hessenberg matrix condition.

* * * * *